US012703702B2

(12) United States Patent
Desai et al.

(10) Patent No.: US 12,703,702 B2
(45) Date of Patent: Aug. 11, 2026

(54) PROCESS FOR THE PREPARATION OF TOFACITINIB AND INTERMEDIATES THEREOF

(71) Applicant: AARTI PHARMALABS LIMITED, Mumbai (IN)

(72) Inventors: Parimal Hasmukhlal Desai, Mumbai (IN); Bharatkumar Surendra Patravale, Thane (IN); Chetan Liladhar Salunke, Thane (IN); Nitin Janardhan Polshetty, Thane (IN)

(73) Assignee: AARTI PHARMALABS LIMITED, Maharashtra (IN)

( * ) Notice: Subject to any disclaimer, the term of this patent is extended or adjusted under 35 U.S.C. 154(b) by 981 days.

(21) Appl. No.: 17/755,514

(22) PCT Filed: Oct. 28, 2020

(86) PCT No.: PCT/IN2020/050910

§ 371 (c)(1),
(2) Date: Apr. 29, 2022

(87) PCT Pub. No.: WO2021/084556

PCT Pub. Date: May 6, 2021

(65) Prior Publication Data

US 2022/0402924 A1 Dec. 22, 2022

(30) Foreign Application Priority Data

Oct. 31, 2019 (IN) ............................ 201921044239

(51) Int. Cl.
*C07D 487/04* (2006.01)

(52) U.S. Cl.
CPC ................................ *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 6,627,754 B2 | 9/2003 | Blumenkopf et al. | |
| 7,301,023 B2 | 11/2007 | Flanagan et al. | |
| 8,309,716 B2 | 11/2012 | Ruggeri et al. | |
| 2016/0297825 A1* | 10/2016 | Bonanomi | C07C 51/412 |

FOREIGN PATENT DOCUMENTS

| | | | | |
|---|---|---|---|---|
| CN | 104530053 A | 4/2015 | | |
| CN | 105693728 A | 6/2016 | | |
| CN | 107793418 A | 3/2018 | | |
| CN | 108358929 A | 8/2018 | | |
| CN | 108794491 A | 11/2018 | | |
| CN | 108948020 A | 12/2018 | | |
| CN | 108997355 A | 12/2018 | | |
| CN | 109516991 A | 3/2019 | | |
| WO | WO-2014102826 A1 * | 7/2014 | | C07D 211/56 |
| WO | WO-2020183295 A1 * | 9/2020 | | C07D 487/04 |

OTHER PUBLICATIONS

International Search Report for PCT/IN2020/050910 dated Mar. 31, 2020 (2 pages).
Patil, Y.S. et al., "An Improved and Efficient Process for the Preparation of Tofacitinib Citrate," Organic Process Research & Development, 18(12), pp. 1714-1720 (2014).
Written Opinion for PCT/IN2020/050910 dated Mar. 31, 2020 (5 pages).
Patil, Yogesh S. et al., "An Improved and Efficient Process for the Preparation of Tofacitinib Citrate," Organic Process Research & Development, 2014 18(12), pp. 1714-1720.
Extended European Search Report for EP Application No. 20881593. 6-1110/ 4051681 PCT/IN2020050910; Dated—Jul. 14, 2023; 129 pages.
International Preliminary Report on Patentability for International Application No. PCT/IN2020/050910; International Filing Date—Oct. 28, 2020; Date of Issuance—May 3, 2022; 2 pages.
Written Opinion of the International Searching Authority for International Application No. PCT/IN2020/050910; International Filing Date—Oct. 28, 2020; Date of Mailing—Dec. 31, 2020, 5 pages.

* cited by examiner

*Primary Examiner* — Sarah Pihonak
*Assistant Examiner* — Mikhail O'donnel Robinson
(74) *Attorney, Agent, or Firm* — CANTOR COLBURN LLP

(57) ABSTRACT

A process for the preparation of high purity tofacitinib, which reduces formation of N-methyl impurity is provided. Novel intermediates used in the process to prepare tofacitinib is also provided. A process for the preparation of tofacitinib (I), comprising the steps of: adding cyanoacetic acid in molar equivalent 0.2-1.2 to compound of formula (IIS), followed by addition of carbodiimide coupling agent of formula (III), optionally reacting tofacitinib base with citric acid is further provided.

21 Claims, No Drawings

PROCESS FOR THE PREPARATION OF TOFACITINIB AND INTERMEDIATES THEREOF

This application is a national stage filing under 35 U.S.C. § 371 of International Application No. PCT/IN2020/050910, filed on Oct. 28, 2020, which claims priority of Indian Patent Application number 201921044239, filed on Oct. 31, 2019. The contents of these applications are each incorporated herein by reference.

FIELD OF THE INVENTION

The present invention generally relates to the field of process chemistry, and more particularly relates to process for preparing of tofacitinib, which reduces formation of N-methyl impurity. The present invention also relates to novel intermediates used in the process to prepare tofacitinib.

BACKGROUND OF THE INVENTION

3-[(3R,4R)-4-methyl-3-[methyl (7H-pyrrolo[2,3-d]pyrimidin-4-yl) amino]piperidin-1-yl]-3-oxopropanenitrile, generically known as tofacitinib, belongs to therapeutic class of janus kinase (JAK) inhibitors and is marketed under the tradename Xeljianx® for the treatment of moderate of severe rheumatoid arthritis, and moderate to severe ulcerative colitis.

Tofacitinib, structurally represented as formula I,

Formula (I)

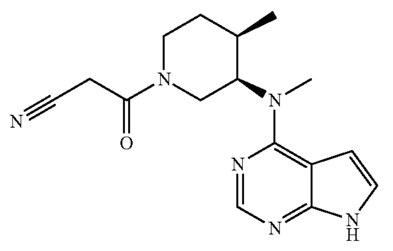

is reported and disclosed in the Indian Pat. No. 241773 along with the monocitrate salt but does not mention any details about the stereochemistry of tofacitinib. Indian Pat. Application No. 737/MUMNP/2011 discloses preparation of chiral tofacitinib, by reacting 4-chloro-pyrrolopyrimidine with tartrate salt of (3R,4R)-1-benzyl-N,4-dimethyl-piperidin-3-amine as schematically shown below.

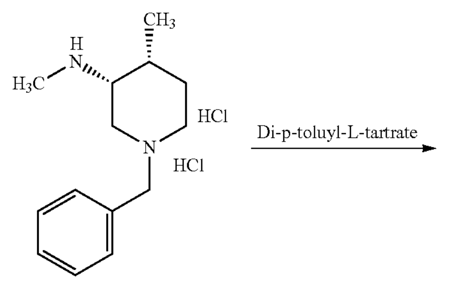

-continued

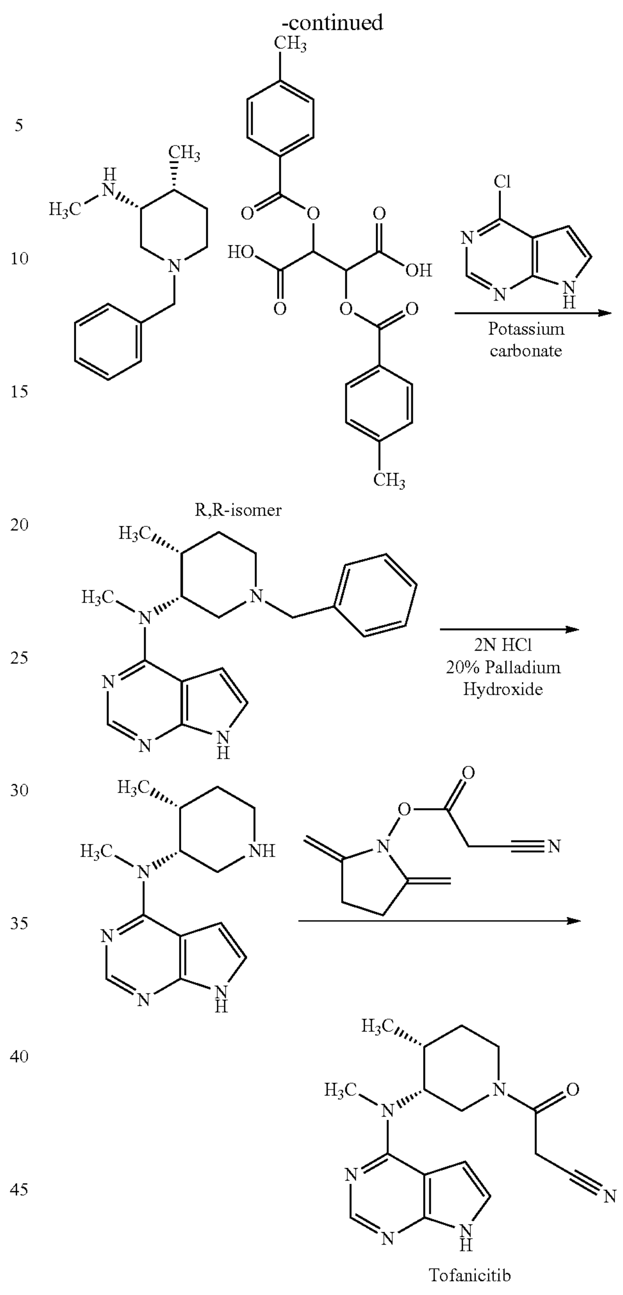

The yield obtained in the coupling of 4-chloro-pyrrolopyrimidine with tartrate salt of (3R,4R)-1-benzyl-N,4-dimethyl-piperidin-3-amine is 54% and the time required for reaction is about 90 hrs., which is difficult to apply for industrial scale up.

Further, the debenzylation of (3R,4R)-(1-benzyl-4-methyl-piperidine-3-yl)-methyl-(7H-pyrrolo[2,3-d]pyrimidine-4-yl)-amine is done using 20% palladium on carbon. The reaction time reported is 2 days. Also, flash chromatography is needed for purification of methyl-((3R,4R)-4-methyl-piperidin-3-yl)-(7H-pyrrolo[2,3-d]pyrimidin-4-yl)-amine.

Indian Pat. Appl. No. 270/DELNP/2008 discloses process for preparing tofacitinib by reacting bis-(3R,4R)-(1-benzyl-4-methyl-piperidine-3-yl)-methylamine di-p-toluoyl-L-tartaric acid with 4-chloro-7-(4-methyl-benzenesulfonyl)-7H-pyrrolo[2,3-d]pyrimidine in presence of potassium carbonate and water at 95-105° C. The coupled product was isolated in acetonitrile and detosylation was carried out in water using sodium hydroxide as a base to form [(3R,4R)-1-benzyl-4-methyl-piperidin-3-yl]-methyl-(7H-pyrrolo[2,3-d]pyrimidin-4-yl)-amine.

Further, the debenzylation is done using 20% palladium hydroxide on carbon in water and IPA mixture in presence of acetic acid and methyl-[(3R,4R)-4-methyl-piperidin-3-yl]-(7H-pyrrolo[2,3-d]pyrimidin-4-yl)-amine was isolated. Additionally, tofacitinib is prepared by reacting methyl-[(3R,4R)-4-methyl-piperidin-3-yl]-(7H-pyrrolo[2,3-d]pyrimidin-4-yl)-amine with ethyl cyano acetate in presence of triethylamine.

Although the '270 application mentions detosylation of (1-benzyl-4-methyl-piperidin-3-yl)-methyl-[7-(toluene-4-sulfonyl)-7H-pyrrolo [2,3-d]pyrimidin-4-yl]-amine in the aqueous medium, the inventors of the present invention observed that substantially in aqueous medium, the reaction does not take place at all. Hence, there is need to provide a suitable solvent for reaction to occur smoothly and yield pure [(3R,4R)-1-benzyl-4-methyl-piperidin-3-yl]-methyl-(7H-pyrrolo [2,3-d]pyrimidin-4-yl)-amine.

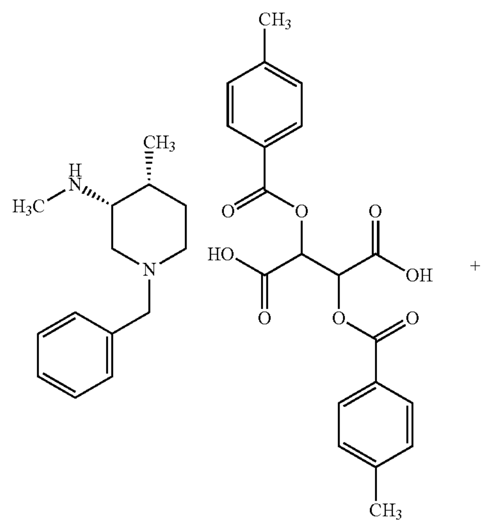

R,R-isomer

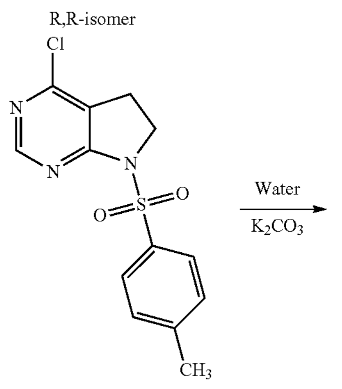

-continued

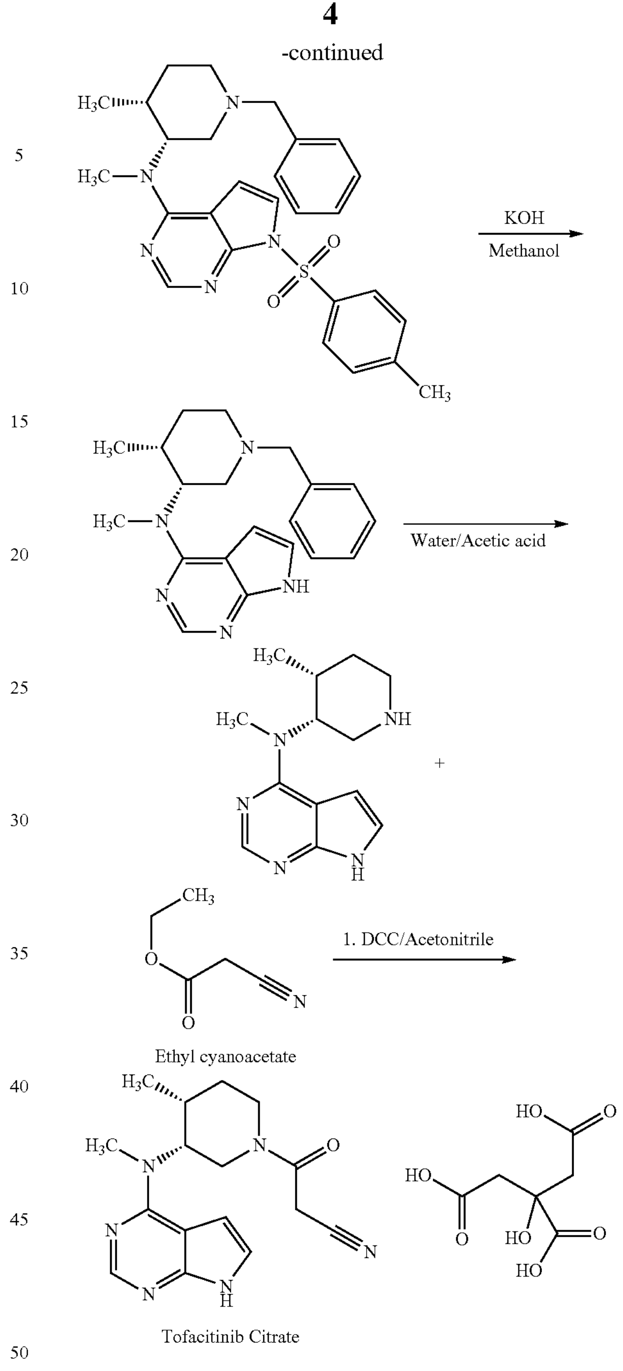

Ethyl cyanoacetate

Tofacitinib Citrate

Also, the isolation of free base [(3R,4R)-1-benzyl-4-methyl-piperidin-3-yl]-methyl-[7-(4-methyl-benzenesulfonyl)-7H-pyrrolo [2,3-d]pyrimidin-4-yl] amine have major problem of yield loss due to many reasons. As pH adjustment is made using hydroxide such as sodium hydroxide, sodium salt of [(3R,4R)-1-benzyl-4-methyl-piperidin-3-yl]-methyl-[7-(4-methyl-benzenesulfonyl)-7H-pyrrolo [2,3-d] pyrimidin-4-yl] amine is formed, which goes in the aqueous layer and hence there is a loss in yield in isolating free base. Also, the free base being highly hygroscopic in nature, during filtration absorbs moisture and upper layer becomes oily and isolation of free base solid becomes difficult.

Hence, there is a need of an alternative improved process which avoids yield loss due to alkali metal salt formation and provides isolation of solid salt which provides highly pure tofacitinib with quantitative yields.

Org. Process Res. Dev. 2014, 18(12), 1714-1720 mentions detosylation of (3R, 4R)-(1-benzyl-4-methylpiperidin-3-yl)methyl-(7-tosylpyrrolo[2,3-d]pyrimidin-4-yl)amine in alcoholic solvents. In the reaction using methanol as a solvent, the reaction mass was cooled and filtered directly without distillation to obtain (3R,4R)-(1-Benzyl-4-methylpiperidin-3-yl)methyl-(7H-pyrrolo[2,3-d]pyrimidin-4-yl) amine with 96% purity.

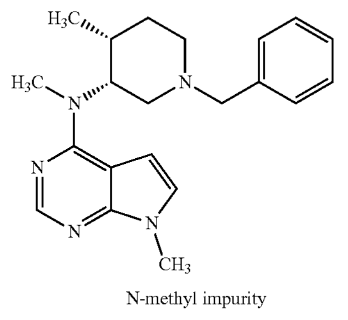 [SMILES: C[C@@H]1CCN(Cc2ccccc2)C[C@@H]1N(C)c1ncnc2c1ccn2C]

N-methyl impurity

However, it is observed that in actual coarse of the reaction in methanol, N-methyl impurity as shown in the structure above is formed up to 6% and is difficult to remove and is carry forwarded in final product, i.e. tofacitinib citrate.

Thus, there is a need to develop an alternative process, which reduces N-methyl impurity formation and provides (3R,4R)-(1-benzyl-4-methylpiperidin-3-yl)methyl-(7H-pyrrolo[2,3-d]pyrimidin-4-yl)amine with higher purity.

SUMMARY OF THE INVENTION

To obviate the drawbacks of above prior art, the present invention provides an industrially viable process for the preparation of high purity tofacitinib, which is of high yield with low synthesis cost, eco-friendly and suitable for industrial scaleup.

The present invention provides a process, which reduces formation of N-methyl impurity during the preparation of tofacitinib.

In one aspect of the present invention, there is provided an improved process for the preparation of tofacitinib (I),

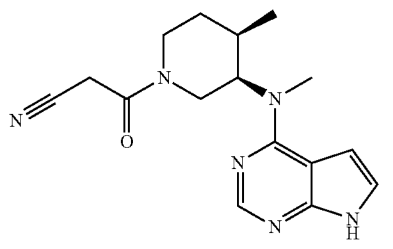 [SMILES: C[C@@H]1CCN(C(=O)CC#N)C[C@@H]1N(C)c1ncnc2[nH]ccc12]

comprising the steps of: adding cyanoacetic acid in molar equivalent 0.2-1.2 to compound of formula (II-S), (II-S)

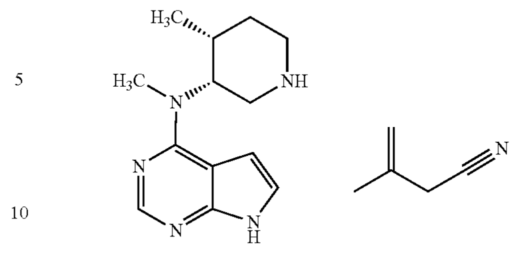

followed by addition of carbodiimide coupling agent of formula (III), (III)

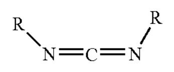

optionally reacting tofacitinib base with citric acid.

In other aspect of the present invention, there is provided a process for preparing compound of formula (II-S).

These and other aspects of the present invention may be understood more readily by reference to the following detailed description of exemplary embodiments of the invention and the examples included therein.

DETAILED DESCRIPTION OF THE INVENTION

The present invention provides a process for the preparation of high purity tofacitinib by reducing formation of N-methyl impurity.

In one embodiment, the present invention provides a process for the preparation of tofacitinib of formula (I) and salt thereof comprising steps of, (a) adding cyanoacetic acid. in molar equivalent 0.2-1.2 to compound of formula (II-S), (II-S)

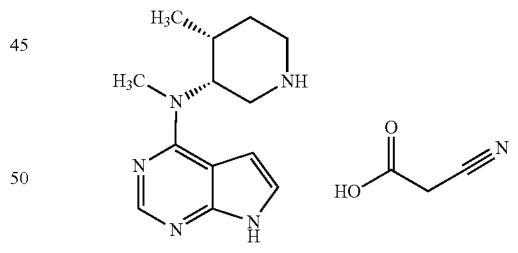

(b) reacting the reaction mixture with carbodiimide coupling agent of formula (III)

(III)

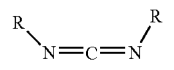

(c) optionally reacting tofacitinib base formed with citric acid, wherein R is selected from cyclohexyl, isopropyl, ethyl, 3-dimethylamino propyl (or its hydrohalide or alkylhalide addition salt), where both R substituent of formula (III) can be same or a combination of above-mentioned groups.

In the process, step (a) is carried out at a room temperature and reaction is carried out in a suitable solvent may be, without limitation, aprotic solvents, esters, ethers, hydrocarbons, halogenated solvents, and ketones.

For example, aprotic solvent used is preferably acetonitrile. Esters may include, but are not limited to, ethyl acetate, and butyl acetate. Ethers may include, but are not limited to, tetrahydrofuran (THF), methyl tertbutyl ether (MTBE), and di-isopropyl ether (DIPE). Hydrocarbon solvents may include, but are not limited to, toluene, xylene, and cyclohexane. Halogenated hydrocarbons may include, but are not limited to, methylene dichloride (MDC), chloroform, 1,2-dichloroethane, and chlorobenzene. Ketone solvents may include, but not limited to, acetone, and methyl isobutyl ketone (MIBK).

Carbodiimide coupling agent used in stage (ii) of the process may include, but not limited to, dicyclohexylcarbiodimide, 1-ethyl-3(3-dimethylamino propyl) carbodiimide, and N, N'-diisopropylcarbodiimide.

The reaction may optionally be carried out in the presence of coupling agent, which may include, but not limited to, hydroxybenzotriazole (HOBt), N-hydroxy-5-norbornene-endo-2,3-dicarboxyimide (HONB), N-hydroxysuccinimide (HOSu), hydroxy-7-azabenzotriazole (HOAt), O-(1H-benzotriazol-1-yl)-tetramethyl uroniumhexafluorophosphate, (HBTU), and 2-(1H-Benzotriazole-1-yl)-1,1,3,3-tetramethylaminium tetrafluoroborate (TBTU).

The reaction is carried out at 0-40° C., preferably at 15-20° C.

Tofacitinib base formed in step (c) may either be isolated or converted to tofacitinib citrate in situ by reacting with citric acid.

In another embodiment, the present invention provides a process for preparation of compound of formula (II-S), wherein the process comprises the steps of:

(ia) reacting compound of formula (VI) with compound of formula (VII) in presence of suitable alkali to form compound of formula (V);

(VI)

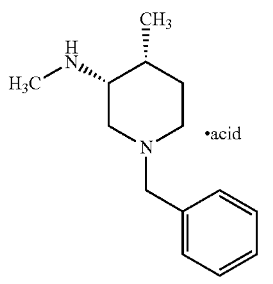

(VII)

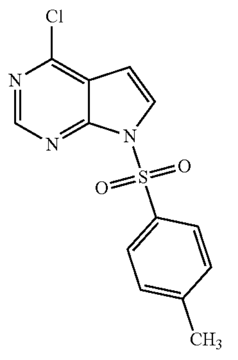

(iia) reacting compound of formula (V) with suitable alkali metal hydroxide, wherein the reaction is carried out in predefined solvent system to form compound of formula (IV)

(V)

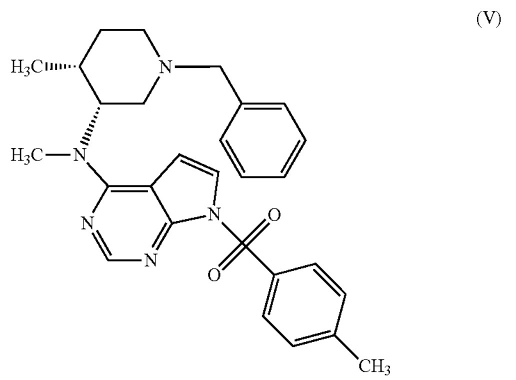

(IV)

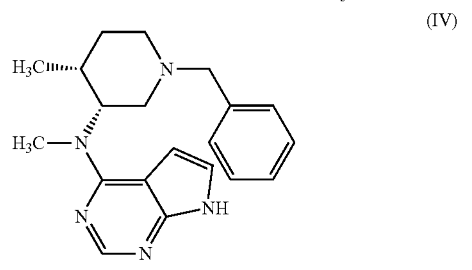

(iiia) hydrogenation of compound of formula (IV) at a pH 3-5 using suitable metal catalyst to form compound of formula (II), (II)

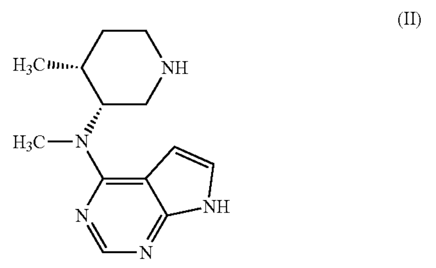 [SMILES: C[C@@H]1CCNC[C@@H]1N(C)c1ncnc2[nH]ccc12]

(iva) without isolation of compound formula (II), adjusting the pH of the reaction mass using organic base like ammonia. The compound (II) is extracted using suitable solvent from reaction mass and adding cyanoacetic acid to form and isolate cyanoacetate salt of formula (II-S).

The organic base used may be selected, without limitation, from ammonia, mono, di or trialkyl amines, such as methylamine, ethylenediamine, dimethylamine, triethyl amine, and diisopropyl ethylamine, aromatic amines, such as pyridine and N, N-dimethyl aniline. The preferred base is ammonia. The solvent used for extraction and cyanoacetate salt formation may include, without limitation, water immiscible solvents like higher alcohols such as 1-butanol, hydrocarbons (toluene, cyclohexane), esters (ethyl acetate, butyl acetate) and ethers (diisopropyl ether, methyl tertiary butyl ether).

The salt is characterized by NMR.

$^1$H NMR (300 MHz, $D_2O$): 7.747 (1H), 6.871-6.861 (1H), 6.168 (1H), 4.420 (1H), 3.463-3.387 (1H), 3.320-3.182

(3H), 3.092-3.031 (2H), 2.909 (3H), 2.015 (1H), 1.879-1.819 (1H), 1.554-1.505 (1H), 0.784-0.761 (3H).

$^{13}C$ APT (300 MHz, D6-DMSO): 166.04 (C), 156.91 (C), 152.13 (C), 150.95 (CH), 121.57 (CH), 118.86 (C), 102.72 (C), 102.01 (CH), 52.67 ($CH_3$), 41.14 ($CH_2$), 38.68 ($CH_2$), 34.23 (CH), 30.18 (CH), 28.89 ($CH_2$), 27.30 ($CH_2$), 12.81 ($CH_3$).

Compound VI used in step (ia) of the process is a salt with suitable acid selected from hydrochloric acid, tartaric acid, ditoluoyl tartaric acid, acetic acid, and sulfuric acid. Alkali used in step (ia) is an inorganic base such as alkali metal carbonates, preferably selected from potassium carbonate and sodium carbonate.

Reaction is carried out at 80-100° C., preferably at 85-95° C., particularly at 90-95° C.

Alkali metal hydroxide used in step (iia) of the process, may include, but not limited to, lithium hydroxide, sodium hydroxide, and potassium hydroxide.

It was observed by the inventors that when the reaction is carried out in water or substantially in aqueous solvent, the reaction does not proceed at all.

Hence alcohol and water solvent system was tried, with various alcoholic solvents like methanol, ethanol or isopropanol. It is observed depending upon the solvent used, N-alkyl impurity is formed in the reaction. Methanol water solvent system was found to work well than other alcoholic solvents.

In a general course of the reaction in step (iia), with methanol solvent, N-methyl impurity is formed, which is around 6-8%. This N-methyl impurity is represented by the below structure.

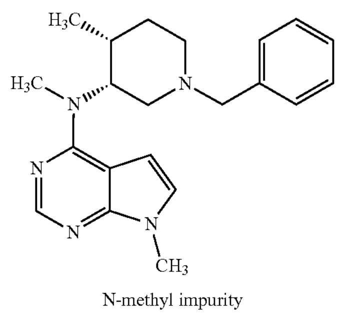 [SMILES: C[C@@H]1CCN(Cc2ccccc2)C[C@@H]1N(C)c1ncnc2c1ccn2C]

N-methyl impurity

The impurity is confirmed by LCMS and NMR.

In LCMS it shows molecular ion [M+H]+ detected at (350 m/z) which corresponds to molecular weight (349).

Proton NMR shows singlet at δ=3.7, which corresponds to N-7 methyl group.

The solvent system used in step (iia) is methanol and water. It is observed that the ratio of methanol and water plays important role in N-methyl impurity formation.

The reaction is studied at different ratio of methanol and water. Below table indicates impact of ratio of methanol and water on N-methyl impurity formation.

TABLE 1

| Solvent | Qty. | Yield | Purity | N-methyl impurity |
|---|---|---|---|---|
| Methanol | 4 V | 91.9% | 90.88% | 6% |
| Methanol:Water | 4 V:1 V | 96.29% | 97.13% | 2% |
| Methanol:Water | 4 V:2 V | Reaction incomplete | 47.69% | Not detected |
| Water | 4 V | Reaction does not proceed | NA | NA |

From Table 1, it is clear that best results are obtained when methanol:water ratio is 4:1. The reaction is carried out at 30-65° C., preferably at 35-45° C.

The metal catalyst used in step (iiia) may include, but not limited to, Palladium (0), Pd on carbon, $Pd(OH)_2$, palladium acetate, platinum oxide, platinum black, Raney nickel and the like. Before adding metal catalyst, pH of the reaction mixture is adjusted to 3-5, preferably 3.5-4.5 using a suitable acid.

The suitable acid used in step (iiia) may preferably include, but not limited to, hydrochloric acid, acetic acid, and sulfuric acid.

The reaction is carried out at 25-60° C., preferably at 45-55° C.

The reaction can be carried out under hydrogen pressure in inert atmosphere. The reaction proceeds well at normal pressure conditions. This is achieved by purging hydrogen gas in the reaction mass.

The additional advantage of purging hydrogen is minimization of dihydro impurity in the reaction. This dihydro impurity is represented by the structure below.

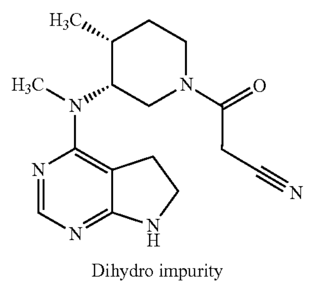 [SMILES: C[C@@H]1CCN(C(=O)CC#N)C[C@@H]1N(C)c1ncnc2c1CCN2]

Dihydro impurity

It is reported in literature and also observed by the inventors that in hydrogenation under pressure, this dihydro impurity is formed. At least 1% of the impurity is formed in the reaction which is carry forwarded in the next step. The impurity is difficult to remove in the next step as well. For the removal, extra purifications are required, which ultimately affects the yield of the final product.

When the hydrogen purging is done and the reaction is carried out at a normal pressure conditions, the formation of dihydro impurity is minimized to below 0.5%. In the next step it can be easily controlled in a single purification.

Ammonia used in step (iva) of the process is aqueous ammonia, gaseous ammonia or liq. ammonia. Use of ammonia instead of alkali metal hydroxide, avoids yield loss due to alkali metal salt formation.

Step (iva) is carried out in a suitable water immiscible solvent like higher alcohols, such as 1-butanol, hydrocarbons, such as toluene and cyclohexane, esters, such as ethyl acetate and butyl acetate, and ethers, such as diisopropyl ether and methyl tertiary butyl ether.

Specific embodiments of the invention will now be demonstrated by reference to the following examples. It should be understood that these examples are disclosed solely by way of illustrating the invention and should not be taken in any way to limit the scope of the present invention.

Example 1

Preparation of N-[(3R,4R)-1-benzyl-4-methyl-3-piperidyl]-N-methyl-7-(p-tolyl sulfonyl) pyrrole[2,3-d]pyrimidin-4-amine (3R,4R)-1-benzyl-N,4-dimethylpiperidin-3-amine dihydrochloride (100 g) was charged to water (100 ml) and the reaction mixture was stirred. Potassium carbonate (376 gm) was charged lot wise to the mixture. The mixture was stirred for 15-20 minutes. 4-chloro-7-[(4-methylphenyl) sulfonyl]-7H-pyrrolo[2,3-d]pyrimidine (132 gm) was charged to the reaction mass and temperature was raised to 90-95° C. The mass was stirred for 18-19 hours at 90-95° C. The mass was cooled to 30-35° C. and the mass was further stirred for 1-1.5 hours. The mass was filtered and suck dried.

MDC (1000 ml) was charged to the compound and stirred to get clear solution. The layer was extracted with water (500 ml×2). The layers were separated, and MDC was distilled off atmospherically. Acetonitrile (50 ml) was charged and temperature was raised to 60-65° C. and stirred for 1-1.5 hours. The slurry was cooled to 30-35° C. and stirred for 1 hr. then filtered and dried under vacuum for 6-7 hours to isolate N-[(3R,4R)-1-benzyl-4-methyl-3-piperidyl]-N-methyl-7-(p-tolylsulfonyl)pyrrolo[2,3-d]pyrimidin-4-amine (155 gm).

Purity: 99.28%

Example 2

Preparation of N-[(3R,4R)-1-benzyl-4-methyl-3-piperidyl]-N-methyl-7H-pyrrolo[2,3-d]pyrimidin-4-amine N-[(3R,4R)-1-benzyl-4-methyl-3-piperidyl]-N-methyl-7-(p-tolylsulfonyl)pyrrolo[2,3-d]pyrimidin-4-amine (100 g) obtained in example 1 was charged to methanol (400 ml) and the mixture was stirred for 15-20 minutes. 6M solution of potassium hydroxide (100 ml) was prepared separately and charged slowly to the reaction mixture by maintaining temperature. The mass was stirred for 1-1.5 hours and temperature was raised to 40° C. The mass was further stirred at 40-45° C. for 19-20 hours. After cooling to 30-35° C., water (500 ml) was charged to the reaction mass and stirred for 1-1.5 hours. The mass was filtered, and the product was washed with water (100 ml).

5% aqueous sodium bicarbonate (500 ml) was charged to the wet solid and the mass was stirred for 1-1.5 hours and filtered. The wet solid was slurried in water (500 ml) at 60-65° C. and filtered hot. The wet solid was charged to acetonitrile (300 ml) and stirred for 1-1.5 hour. The mass was filtered and dried under vacuum at 50-55° C. for 6-7 hours. N-[(3R,4R)-1-benzyl-4-methyl-3-piperidyl]-N-methyl-7H-pyrrolo [2,3-d]pyrimidin-4-amine (65 gm) was isolated.

Purity: 97.13%

Example 3

N-methyl-N-[(3R,4R)-4-methyl-3-piperidyl]-7H-pyrrolo[2,3-d]pyrimidin-4-amine cyano acetate salt N-[(3R,4R)-1-benzyl-4-methyl-3-piperidyl]-N-methyl-7H-pyrrolo[2,3-d]pyrimidin-4-amine (100 g) obtained in example 2 was charged to the mixture of water (450 ml) and acetic acid (89.45 gm). The mixture was stirred for 50-60 minutes, filtered and washed with water (50 ml). In an inert atmosphere, 5% pd/C (20 gm) was charged to the filtrate and the mixture was stirred for 18-24 hours at 40-50° C. and under hydrogen. The mass was cooled to 20-25° C. filtered and pH was adjusted to 9 with ammonia. The temperature was raised to 30-35° C. and n-butanol (500 ml) was charged. The layers were separated and to the organic layer cyanoacetic acid (25.36 gm) was charged. The mass was stirred, and the solvent was distilled off under vacuum. The mass was cooled to 30-35° C. and acetonitrile (300 ml) was charged. The temperature was raised to 55-60° C. and mass was cooled to 30-35° C. and stirred for 1 hr. then as stirred for 1-1.5 hours. filtered and dried under vacuum at 50-55° C. for 7-8 hours. N-methyl-N-[(3R,4R)-4-methyl-3-piperidyl]-7H-pyrrolo[2,3-d]pyrimidin-4-amine cyano acetate salt (86.5 gm) was isolated.

Purity: 99.50%

Example 4

N-methyl-N-[(3R,4R)-4-methyl-3-piperidyl]-7H-pyrrolo[2,3-d]pyrimidin-4-amine cyanoacetate salt N-[(3R,4R)-1-benzyl-4-methyl-3-piperidyl]-N-methyl-7H-pyrrolo[2,3-d]pyrimidin-4-amine (500 g) obtained in example 2 was charged to the mixture of water (450 ml) and pH of the reaction mixture was adjusted to 3.5-4.5 using hydrochloric acid at room temperature. The reaction mixture was stirred for 30-60 minutes. The mass was filtered and washed with water. 5% pd/C (10 gm) was charged to the filtrate.

Hydrogen gas was purged in the mass and the temperature was raised to 40-45° C. The mass was stirred for 12-18 hours at 40-45° C. The mass was cooled to 20-25° C. filtered and pH was adjusted to 9 with ammonia. The temperature was raised to 30-35° C. and n-butanol (500 ml) was charged. The layers were separated and to the organic layer cyanoacetic acid (25.36 gm) was charged. The mass was stirred solvent was distilled off under vacuum. The mass was cooled to 30-35° C. and acetonitrile (300 ml) was charged. The temperature was raised to 55-60° C. and mass was stirred for 1-1.5 hours. The mass was cooled to 30-35° C. and stirred for 1 hr. then filtered and dried under vacuum at 50-55° C. for 7-8 hours. N-methyl-N-[(3R,4R)-4-methyl-3-piperidyl]-7H-pyrrolo[2,3-d]pyrimidin-4-amine cyano acetate salt (43.3 gm) was isolated.

Purity: 99.50%

N-methyl impurity—0.5%

Example 5

N-methyl-N-[(3R,4R)-4-methyl-3-piperidyl]-7H-pyrrolo[2,3-d]pyrimidin-4-amine

N-[(3R,4R)-1-benzyl-4-methyl-3-piperidyl]-N-methyl-7H-pyrrolo[2,3-d]pyrimidin-4-amine (100 g) obtained in example 2 was charged to water (450 ml) and pH of the reaction mixture was adjusted to 3.5-4.5 using hydrochloric acid at room temperature. The reaction mixture was stirred for 30-60 minutes. The mass was filtered and washed with water. 5% pd/C (10 gm) was charged to the filtrate. Hydrogen gas was purged in the mass and the temperature was raised to 45-50° C. The mass was stirred for 10-12 hours at 45-50° C. The mass was cooled to 30-35° C., filtered and cooled to 15 to 20° C. The pH of the reaction mass was adjusted to 9 with ammonia. The temperature was raised to 30-35° C. and n-butanol (500 ml) was charged. The mass was stirred, and the layers were separated. The organic layer was distilled under vacuum and the mass was cooled.

Acetonitrile (300 ml) was charged to the reaction mass and temperature was raised to 60-65° C. The mass was stirred for 1-1.5 hours. The mass was cooled to 25-30° C. and stirred for 2-3 hours. The mass was filtered and washed with acetonitrile (100 ml). The product was suck dried and N-methyl-N-[(3R,4R)-4-methyl-3-piperidyl]-7H-pyrrolo[2,3-d]pyrimidin-4-amine was isolated as wet solid.

N-methyl impurity: 1%

Dihydro impurity—Not detected

Example 6

Purification of N-methyl-N-[(3R,4R)-4-methyl-3-piperidyl]-7H-pyrrolo[2,3-d]pyrimidin-4-amine Acetonitrile (100 ml) was charged to N-methyl-N-[(3R,4R)-4-methyl-3-piperidyl]-7H-pyrrolo[2,3-d]pyrimidin-4-amine obtained in example 5 at 30-35° C. The temperature of the reaction mixture was raised to 60-65° C. and the mixture was stirred for 1-1.5 hours. The mass was cooled to 25-30° C. and stirred for 2-3 hours. The mass was filtered and washed with acetonitrile (100 ml). N-methyl-N-[(3R,4R)-4-methyl-3-piperidyl]-7H-pyrrolo[2,3-d]pyrimidin-4-amine was isolated as wet solid N-methyl impurity: 0.5%

Dihydro impurity—Not detected

Example 7

N-methyl-N-[(3R,4R)-4-methyl-3-piperidyl]-7H-pyrrolo[2,3-d]pyrimidin-4-amine cyano acetate salt Acetonitrile (200 ml) was charged to N-methyl-N-[(3R,4R)-4-methyl-3-piperidyl]-7H-pyrrolo[2,3-d]pyrimidin-4-amine obtained in example 6 at 30-35° C. The reaction mixture was stirred for 1-1.5 hours. Solution of cyanoacetic acid (prepared by dissolving 25.36 gm cyanoacetic acid in 100 ml acetonitrile) was charged to above reaction mixture. The temperature was raised to 60-65° C. and the mass was stirred for 1.5-2 hours. The mixture was cooled to 25-30° C. and stirred for 2-3 hours. The mass was filtered and washed with acetonitrile (100 ml) and suck dried. The product was dried under vacuum for 5-6 hours.

N-methyl-N-[(3R,4R)-4-methyl-3-piperidyl]-7H-pyrrolo[2,3-d]pyrimidin-4-amine cyano acetate salt (79 gm) was isolated. (80% yield)

N-methyl impurity—Not detected

Dihydro impurity—Not detected

Example 8

Tofacitinib Citrate

N-methyl-N-[(3R,4R)-4-methyl-3-piperidyl]-7H-pyrrolo[2,3-d]pyrimidin-4-amine cyano acetate salt (100 gm) obtained from example 4, was charged to acetonitrile (400 ml). Cyanoacetic acid (12.87 g) was charged to the reaction mixture and the reaction mass was cooled to 15-20° C. A solution of DCC (93.66 gm) in acetonitrile (300 ml) was charged at 15-20° C. and the reaction mass was stirred for 1-1.5 hours at same temperature.

After completion of reaction, aqueous ammonia (30 ml) was added to reaction mass and stirred for 1-1.5 hrs. The reaction mass was then filtered and washed with acetonitrile (200 ml). The filtrate was decolorized using carbon treatment and charged to a clean RBF. The temperature was raised to 70-75° C. and a solution of citric acid (140 gm) in water (150 ml) was added to reaction mass. The mass was stirred for 1-1.5 hours. The mass was cooled to 25-30° C. and the mass was stirred further for 2-2.5 hours. The mass was filtered and the precipitate charged to acetonitrile (1470 ml) and water (630 ml) was added to the solution. The temperature was raised to 70-75° C. and stirred for 2-2.5 hours. The reaction mass was cooled to 20-30° C. and stirred at this temperature for 1-1.5 hours. The mass was filtered, and product washed with acetonitrile (150 ml) and dried under vacuum at 65-70° C. for 7-8 hours.

Tofacitinib citrate (125 g) was isolated as a white to off-white powder.

Purity: 99.90%

N-methyl impurity—Not detected

Dihydro impurity—Not detected

We claim:

1. A process for the preparation of tofacitinib of formula (I) and salt thereof

Formula (I)

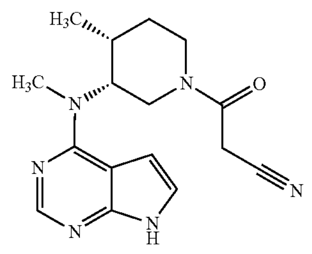

comprising the steps of:

(a) preparing a compound for formula (II-S)

(II-S)

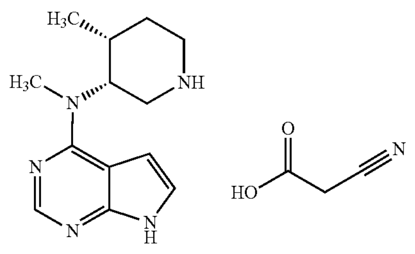

(ia) by reacting a compound of formula (VI) with a compound of formula (VII) in presence of an inorganic base at 80-100° C. to form a compound of formula (V);

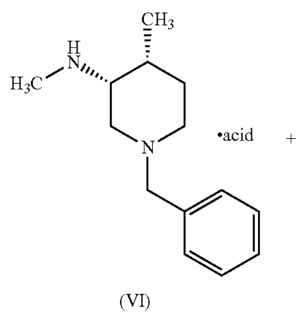

•acid +

(VI)

-continued

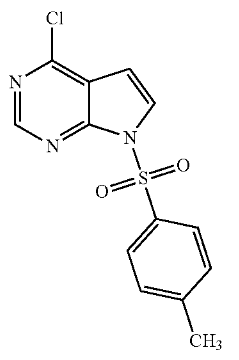

(VII)

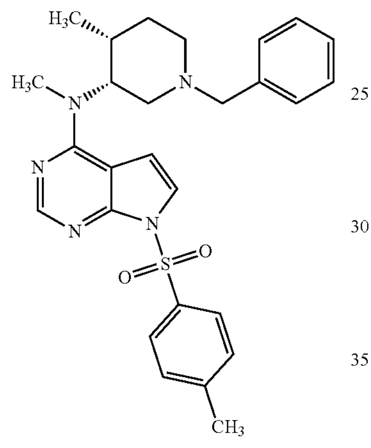

(V)

(iia) reacting the compound of formula (V) with an alkali metal hydroxide, wherein the reaction is carried out at 30-65° C. in a solvent system to form a compound of formula (IV);

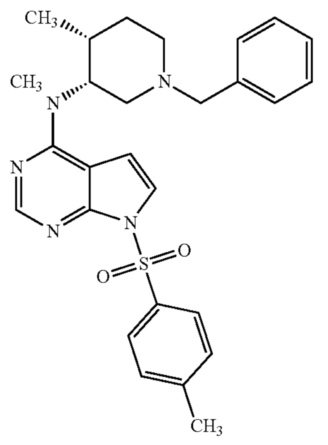

(V)

-continued

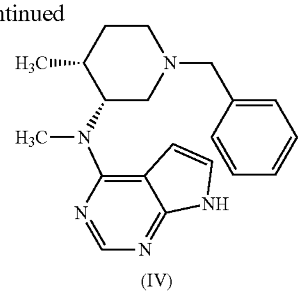

(IV)

(iiia) hydrogenation of the compound of formula (IV) at a pH 3-5 using a metal catalyst at 25-60° C. to form a compound of formula (II);

(II)

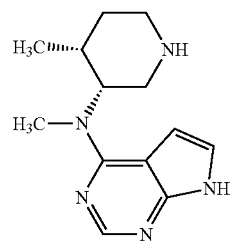

(iva) adding cyanoacetic acid to the compound of formula (II) to form the compound of formula (II-S);

(b) adding cyanoacetic acid in a molar equivalent 0.2-1.2 to compound of formula (II-S), (II-S)

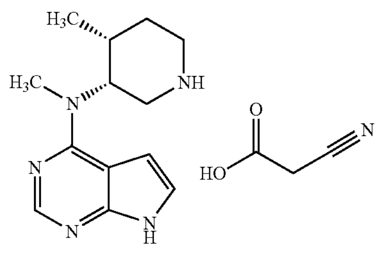

(c) reacting the reaction mixture with carbodiimide of formula (III) at 0-40° C. in the presence of a coupling agent of formula (III) to form the compound of formula (I), (III)

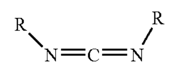

wherein R is selected from cyclohexyl, isopropyl, ethyl, 3-dimethylamino propyl or its hydrohalide or alkylhalide addition salt.

2. The process as claimed in claim 1, wherein step (b) is carried out at a room temperature.

3. The process as claimed in claim 1, wherein step (b) is carried out in a solvent selected from aprotic solvent, hydrocarbon, ester, ether, halogenated solvent, and ketone.

4. The process as claimed in claim 1, wherein carbodiimide of formula (III) is selected from dicyclohexylcarbiodimide, 1-ethyl-3-(3-dimethylaminopropyl) carbodiimide, and N,N'-diisopropylcarbodiimide.

5. The process as claimed in claim 1, wherein the coupling agent is selected from hydroxybenzotriazole (HOBt), N-hydroxy-5-norbornene-endo-2,3-dicarboxyimide (HONB), N-hydroxysuccinimide (HOSu), hydroxy-7-azabenzotriazole (HOAt), O-(1H-benzotriazol-1-yl)-tetramethyl uroniumhexafluorophosphate, (HBTU), and TBTU.

6. The process as claimed in claim 1, wherein tofacitinib formed in step (c) is reacted with citric acid to obtain tofacitinib citrate.

7. A process for the preparation of compound of formula (II-S)

(II-S)

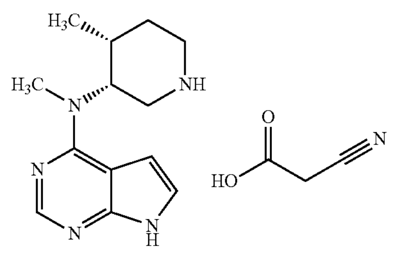

comprising the steps of:

(ia) reacting a compound of formula (VI) with a compound of formula (VII) in presence of an inorganic base at 80-100° C. to form a compound of formula (V);

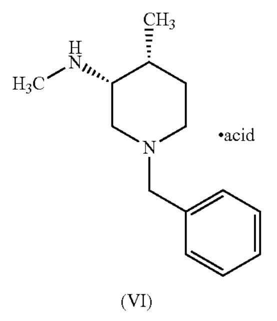

(VI)

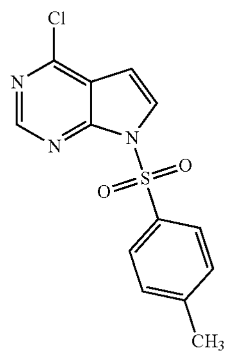

(VII)

-continued

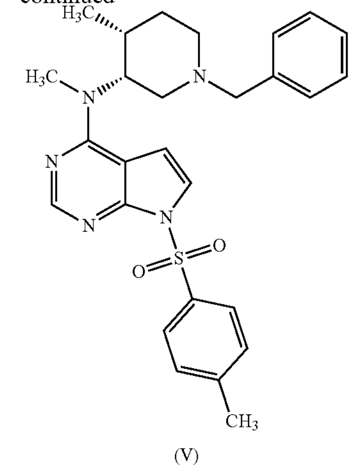

(V)

(iia) reacting the compound of formula (V) with an alkali metal hydroxide, wherein the reaction is carried out at 30-65° C. in a solvent system to form a compound of formula (IV);

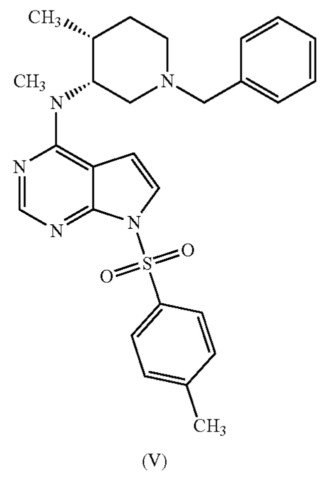

(V)

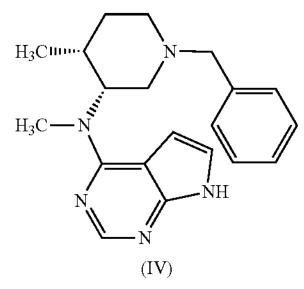

(IV)

(iiia) hydrogenation of the compound of formula (IV) at a pH 3-5 using a metal catalyst at 25-60° C. to form a compound of formula (II) in a mass;

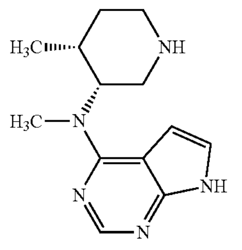

(II)

(iva) adjusting the pH reaction of the mass using an organic base;

(va) extracting the compound of formula (II) using a solvent from the reaction mass;

(via) adding cyanoacetic acid to form the compound of formula (II-S).

8. The process as claimed in claim 7, wherein the compound of formula VI is a salt with an acid selected from hydrochloric acid, tartaric acid, ditoluoyl tartaric acid, acetic acid, and sulfuric acid.

9. The process as claimed in claim 7, wherein the organic base is an alkali metal carbonate.

10. The process as claimed in claim 7, wherein the alkali metal hydroxide is selected lithium hydroxide, sodium hydroxide, and potassium hydroxide.

11. The process as claimed in claim 7, wherein the solvent system is a mixture of water and an alcohol selected from methanol, ethanol, and isopropanol.

12. The process as claimed in claim 11, wherein the solvent system is a mixture of water and methanol.

13. The process as claimed in claim 7, wherein the metal catalyst is selected from the Palladium (0), Pd on carbon, Pd (OH) 2, palladium acetate, platinum oxide, platinum black, and Raney nickel.

14. The process as claimed in claim 7, wherein the pH in step (iiia) is adjusted using an acid selected from hydrochloric acid, acetic acid, and sulfuric acid.

15. The process as claimed in claim 7, wherein the organic base is selected from ammonia, mono-, di-, and trialkyl amines.

16. The process as claimed in claim 15, wherein the organic base is ammonia selected from aqueous ammonia, gaseous ammonia, and liquid ammonia.

17. The process as claimed in claim 7, wherein the solvent in step (va) is a water immiscible solvent.

18. The process as claimed in claim 17, wherein the solvent is selected from alcohol, hydrocarbon, ester, and ether.

19. The process as claimed in claim 7, wherein hydrogen gas is purged in the reaction mixture after the hydrogenation of the compound of formula (IV).

20. A composition comprising tofacitinib citrate free from N-methyl impurity and dihydro impurity.

21. The composition of claim 20 wherein the composition comprises less than 0.5% N-methyl impurity.

* * * * *